United States Patent
Hannoun-Levi et al.

(10) Patent No.: US 8,834,339 B2
(45) Date of Patent: Sep. 16, 2014

(54) ASSEMBLY FOR PERFORMING BRACHYTHERAPY TREATMENT OF A TUMOUR TISSUE IN AN ANIMAL BODY

(75) Inventors: Jean-Michel Hannoun-Levi, Nice (FR); Cor Van De Wardt, Kesteren (NL); Arie Luite Visscher, Driebergen (NL); Dirk Binnekamp, Borne (NL)

(73) Assignee: Nucletron Operations B.V. (NL)

( * ) Notice: Subject to any disclaimer, the term of this patent is extended or adjusted under 35 U.S.C. 154(b) by 445 days.

(21) Appl. No.: 13/120,282

(22) PCT Filed: Sep. 23, 2009

(86) PCT No.: PCT/NL2009/000187
§ 371 (c)(1),
(2), (4) Date: May 26, 2011

(87) PCT Pub. No.: WO2010/036103
PCT Pub. Date: Apr. 1, 2010

(65) Prior Publication Data
US 2011/0224478 A1 Sep. 15, 2011

Related U.S. Application Data

(60) Provisional application No. 61/100,132, filed on Sep. 25, 2008.

(30) Foreign Application Priority Data

Sep. 23, 2008 (NL) .................................... 1035971

(51) Int. Cl.
*A61N 5/00* (2006.01)
*A61N 5/10* (2006.01)
(52) U.S. Cl.
CPC ....... *A61N 5/1016* (2013.01); *A61N 2005/1012* (2013.01)

USPC ............................................................ 600/6
(58) Field of Classification Search
USPC ............ 600/1–7; 604/57, 62, 93.01, 158, 906
See application file for complete search history.

(56) References Cited

U.S. PATENT DOCUMENTS 3,312,128 A    4/1967  Wasson
4,586,490 A *  5/1986  Katz ................................. 600/3
(Continued)

FOREIGN PATENT DOCUMENTS

DE    845558    8/1952
EP    1806161 A1    7/2007

OTHER PUBLICATIONS

Definition of "tubular"; 2003.*
International Search Report from PCT/NL2009/000187, mailed Mar. 23, 2011 (5 pgs.).

(Continued)

*Primary Examiner* — John Lacyk
(74) *Attorney, Agent, or Firm* — Finnegan, Henderson, Farabow, Garrett & Dunner, LLP (57) ABSTRACT

This invention relates to an assembly for performing brachytherapy treatment of tumour tissue in an animal body comprising at least a longitudinally extending intracavitary component and at least a guiding unit which extends at least partly parallel to said intracavitary component. Said guiding unit comprises at least one interstitial needle for guiding a radiation source into the tumour tissue. Said guiding unit is tubular over at least a longitudinal distance sufficient that in use a proximal end of said guiding unit is situated outside said body to be treated, while a distal end of said guiding unit is situated in situ close to or adjacent the tumour tissue.

13 Claims, 10 Drawing Sheets

(56) References Cited

U.S. PATENT DOCUMENTS

| | | | |
|---|---|---|---|
| 4,998,912 A * | 3/1991 | Scarbrough et al. | 600/6 |
| 5,012,357 A * | 4/1991 | Schoeppel et al. | 378/65 |
| 5,161,534 A | 11/1992 | Berthiaume | |
| 5,217,438 A | 6/1993 | Davis et al. | |
| 5,505,714 A | 4/1996 | Dassa et al. | |
| 5,931,786 A * | 8/1999 | Whitmore et al. | 600/459 |
| 5,938,583 A * | 8/1999 | Grimm | 600/7 |
| 6,641,518 B2 * | 11/2003 | Wolfson et al. | 600/6 |
| 2006/0116546 A1 * | 6/2006 | Eng | 600/3 |
| 2008/0071215 A1 * | 3/2008 | Woods et al. | 604/116 |

OTHER PUBLICATIONS

Christian Kirisits, et al., "The Vienna Applicator for Combined Intracavitary and Interstitial Brachytherapy of Cervical Cancer. Design, Application, Treatment Planning, and Dosimetric Results," Int. J. Radiation Oncology Biol. Phys., vol. 65, No. 2, pp. 624-630, 2006.

Johannes C.A. Dimopoulos, M.D. et al., "The Vienna Applicator for Combined Intracavitary and Interstitial Brachytherapy of Cervical Cancer: Clinical Feasibility and Preliminary Results," Int. J. Radiation Oncology Biol. Phys., vol. 65, No. 1, pp. 83-90, 2006.

* cited by examiner

ASSEMBLY FOR PERFORMING BRACHYTHERAPY TREATMENT OF A TUMOUR TISSUE IN AN ANIMAL BODY

This is a National Phase of PCT Application No. PCT/NL09/000187, filed Sep. 23, 2009, which claims priority of Netherlands Application No. 1035971, filed Sep. 23, 2008, and U.S. Provisional Application No. 61/100,132, filed Sep. 25, 2008, all of which are incorporated herein by reference.

This invention relates to an assembly for performing brachytherapy treatment of tumour tissue in an animal body comprising a longitudinally extending intracavitary component and a guiding unit which guiding unit is connectable to said intracavitary component such that the guiding unit extends at least partly parallel with said intracavitary component, wherein said guiding unit comprises at least one interstitial needle for delivering treatment to the tumour tissue.

The invention further relates to a guiding unit for performing brachytherapy treatment of tumour tissue in an animal body comprising at least one interstitial needle and a guiding unit for guiding said interstitial needle.

The invention further relates to a method for performing brachytherapy treatment of tumour tissue in an animal body comprising the steps of
i) assessment of at least one tumour,
ii) inserting an intracavitary component at least partly in a body cavity near the tumour,
iii) connecting a guiding unit comprising at least one needle with said intracavitary component for forming an assembly,
iv) further insertion of said assembly into said cavity such that said assembly is in position for treatment of the tumour.

Assemblies including, interstitial needles are known in the medical field and are suitable for treatment of carcinoma of the cervix and/or endometrium. One known assembly (also known or referred to as a "Vienna Ring") comprises a longitudinally extending intracavitary component, e.g. an intrauterine tube comprising at least partly a radioactive source. Further, the known assembly comprises a guiding unit in the form of a ring comprising holes for guiding moveable interstitial needles. These guide holes allow placement of interstitial needles using the ring as a needle template. The addition of interstitial needles makes it possible to achieve asymmetric alteration of the dose distribution to a tumour.

The known assembly combines interstitial brachytherapy with intracavitary brachytherapy.

During interstitial brachytherapy treatment radioactive sources are inserted into tissue of the human or animal body to be treated, whilst during intracavitary brachytherapy treatment radioactive sources are inserted inside a pre-existing body cavity. With interstitial and intracavity brachytherapy an active radiation source is used to administer what is generally known as High Dose Rate (HDR) treatment. In HDR treatment the radiation source is guided into the tissue or cavity for one or more periods by means of a needle or catheter and is always contained within a closed capsule so it never comes into direct contact with the tissue.

In the known assembly the intracavitary component is inserted first with the distal end in a patient's body cavity. The ring portion then has to be slid over the intracavitary component. In order to insert the ring into said cavity it has to be slid in sideways or at a shallow angle. As a result of this method of insertion of the ring, the needles have to be inserted once the assembly is in situ, e.g. in the vagina. Therefore, placement of the needles into the known assembly requires considerable skill, beyond the capabilities of many brachytherapists. As a result the known assembly is not widely used, despite its positive medical results in effective treatment of cancer.

It is therefore an object of the present invention to achieve an assembly for effective treatment of cancer with interstitial brachytherapy and intracavitary brachytherapy, wherein insertion of the assembly does not require considerable skill.

This object is achieved with the assembly according to the present invention in that said guiding unit is tubular over at least a longitudinal distance sufficient that in use a proximal end of said guiding unit is situated outside said body to be treated, while a distal end of said guiding unit is situated in situ.

An advantage of using such a guiding unit, is that the needle can be placed at a convenient time, way and place whether it is before inserting the assembly partly into a body cavity or after inserting the assembly into a body cavity. Further, the needle is protected by the guiding unit, especially at the position where the assembly goes into a body to be treated.

For the treatment, said longitudinally extending intracavitary component, e.g. an intrauterine tube, is inserted into a cavity, e.g. a uterine canal, and placed in the area to be treated. Once the distal end of the intracavitary component and the distal end of the guiding unit are in position on the site to be treated, i.e. in situ, the interstitial needles which may be at a proximal end of the guiding unit, may be either inserted and/or pushed further into position in the tumour site. This is easily achieved because in normal use the proximal end of the guiding unit is always situated outside the body.

An advantageous embodiment of the assembly according to the present invention is characterised in that said tubular guiding unit is provided with at least one guide for guiding an interstitial needle between said proximal end and said distal end.

It is clearly a much easier procedure to use a tubular guiding unit containing needle guides with proximal ends that in use are located outside a body than to try to insert the needles in guiding holes in a ring, which ring has been placed inside a body. As the proximal ends of the guides of the guiding unit of the assembly according to the present invention are always accessible outside the body, this makes assembling of interstitial needles or bringing them in position after insertion easy for an operator.

An alternative procedure is to assemble the guiding unit and needles before insertion into the patient. This latter alternative was not possible with the prior art ring as the needles were not protected against kinking during insertion into a patient's cavity.

The tubular guiding unit of the assembly according to the invention is only partly inserted into a patient's body. In a preferred embodiment said guiding unit will have a cylindrical shape with a centre line parallel to or along the centre line of the intracavitary component, wherein more than one needle and corresponding guides are available to perform interstitial brachytherapy.

The intracavitary component as discussed in this document is also known as a tandem, or intrauterine tube.

In a preferred embodiment said guiding unit comprises a first part and a second part, wherein the second part forms an angle with the first part.

It has been noticed that tumours do not normally grow symmetrically around a cavity such as the vaginal canal or body part such as the cervix. Therefore, the angled parts facilitate the positioning of the distal ends of the guiding unit such that it is ensured that the needles can be inserted into the tumour. The first and second part can be formed as one piece, such that no joints or transitions are present, which can be preferred from an hygienic perspective.

It is possible that the second part is made in different configurations to change the inclination angle between the first part and the second part between 0 degrees and 80 degrees. Preferably, at least four standards of the second part are available, one being straight and the others forming an angle of 30, 45 or 60 degrees. Of course any other angle can be chosen if convenient. Further, it is advantageous that the first and second part of said guiding unit are detachably coupled with each other. In this way an angle suited for every patient can be assembled by means of the first and second part. Additionally, the components could be available in different lengths to accommodate different sizes of patients. Further, if these parts are reused, they are easier to sterilize.

Further, said interstitial needle is preferably flexible in order to follow said angle between the first and the second part of said guiding unit. Preferably, an interstitial needle is made of plastic material such that these needles are flexible and relatively cheap making them suited for single-use. During moulding of these plastic needles markers can be put into said needles for making them CT and/or MRI compatible.

An advantageous embodiment of the assembly according to the present invention is characterised in that on said guiding unit a template can be detachably coupled which template is provided with at least a guiding support for guiding at least an additional interstitial needle.

Said template comprises for example a ring to be coupled over the guiding unit and a guiding support for supporting and guiding at least one interstitial needle. The template is not moved into a body cavity. In this way at least one additional needle for treatment can be inserted through the skin of a patient into tumour tissue. Simultaneously said tumour tissue can also be treated with said intracavitary component and with the interstitial needles of the guiding unit both situated inside a cavity of a patient's body. The template comprising the additional needles can be used optionally to increase the number of needles and to reach treatment sites from outside a cavity for example the paravaginal region.

In a further embodiment at least parts of the assembly are provided with markers for making the assembly Computed Tomography (CT) and/or Magnetic Resonance Imaging (MRI) compatible. Most parts of the assembly according to the present invention can be made of bio-compatible plastic material, e.g. the guiding unit. A drawback of plastic material is that this material is not visible on a CT image or MRI images of body cavities. To be able to track said parts of the assembly, markers are provided on or in these parts of the assembly.

A further object of the invention is to provide an easy to use guiding unit for performing brachytherapy.

This object is reached with the guiding unit according to the present invention in that said guiding unit is tubular wherein said tubular guiding unit is provided with at least one guide for guiding an interstitial needle between a proximal end of the tubular guiding unit and a distal end of the tubular guiding unit.

Such a guiding unit can be configured and dimensioned to be used with existing tandems suited to be used with a ring. Using such a guiding unit provides the same advantages as described with regard to said assembly. Any feature or any combination of features mentioned in any depending claim of independent claim 1 or mentioned somewhere else in this document, and which feature(s) is applicable to said guiding unit is considered to form part of the guiding unit as described above.

A further object of the invention is to provide an easy to use method for performing interstitial and intracavity brachytherapy.

This object is reached in that said guiding unit is tubular over at least a longitudinal distance sufficient that in use a proximal end of said guiding unit is situated outside a body to be treated, while a distal end of said guiding unit is situated in situ, and said method comprises in addition to steps i)-iv), a step of:

v) using said guiding unit for guiding said interstitial needle to a position for treatment of the tumour.

Such a method lowers the skills required for an operator to use an assembly combining interstitial brachytherapy with intracavitary brachytherapy.

In a specific embodiment the step of inserting said needle into said guiding unit is performed before connecting said guiding unit on said intracavitary component.

As the needles are protected against kinking by means of the tubular guiding unit during insertion into a cavity, there are no objections inserting the needles before coupling and inserting the assembly into a patient's cavity.

In an alternative embodiment inserting said needle into said guiding unit is performed after connecting said guiding unit on said intracavitary component or inserting said needle into said guiding unit is performed after further insertion of said assembly into said cavity, wherein said intracavitary component and the guiding unit are in position for treatment of the tumour.

Further, the method may comprise the step of providing on said tubular guiding unit a template with at least one additional interstitial needle, wherein with this additional needle an additional interstitial treatment is to be performed.

Performing brachytherapy with an intracavity component and the interstitial needles of the guiding unit and the template, of which one is positioned inside a body and the template is positioned outside a body give excellent results in treatment of specific tumours.

An additional needle will be passed through the skin into tumour tissue for performing additional interstitial brachytherapy.

The use of a template according to the present invention can in principle be used with any known applicator. Therefore, it is possible to use a template according to the present invention without a tubular guiding unit as described above, wherein said template is coupled with a different component, e.g. to the intracavity component.

The invention will now be described in more detail with reference to a drawing which drawing shows in.

In the following detailed description with reference to the accompanying figures identical components of the embodiments shown will be indicated with identical reference numerals.

Figure 1:
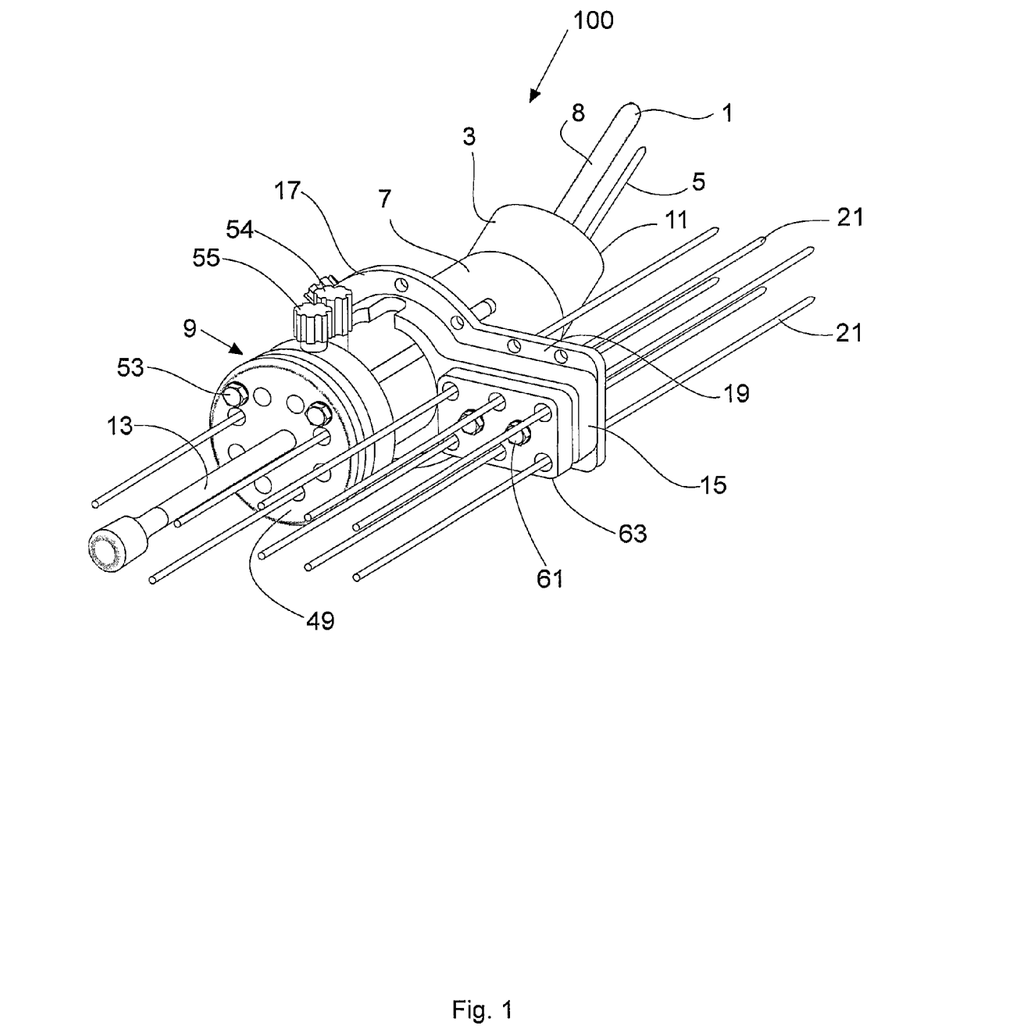
FIG. 1 an embodiment of an assembly according to the invention.

In FIG. 1 a perspective view of an assembly 100 according to the present invention for performing brachytherapy is shown. Said assembly comprises an intracavitary component 1 and a guiding unit 7. The guiding unit 7 is connectable to said intracavitary component 1. Said guiding unit 7 comprises at least one interstitial needle 5 and guiding means for guiding said interstitial needle. Said guiding unit 7 is tubular, in the embodiment shown cylindrical, over at least a longitudinal distance sufficient that in use a proximal end 9 of said guiding unit 7 is situated outside a body to be treated, while a distal end 11 of said guiding unit 7 is situated in situ inside the body cavity.

FIG. 1 shows further a template 15 comprising a ring 17 to be coupled over the guiding unit 7 and a guiding support 19 for supporting and guiding additional interstitial needles.

FIGS. 2-5 show all components for forming an assembly according to the present invention. Further, FIGS. 6a and 6b show a top view and a cross section of the assembly 100 according to the present invention.

Figure 2:
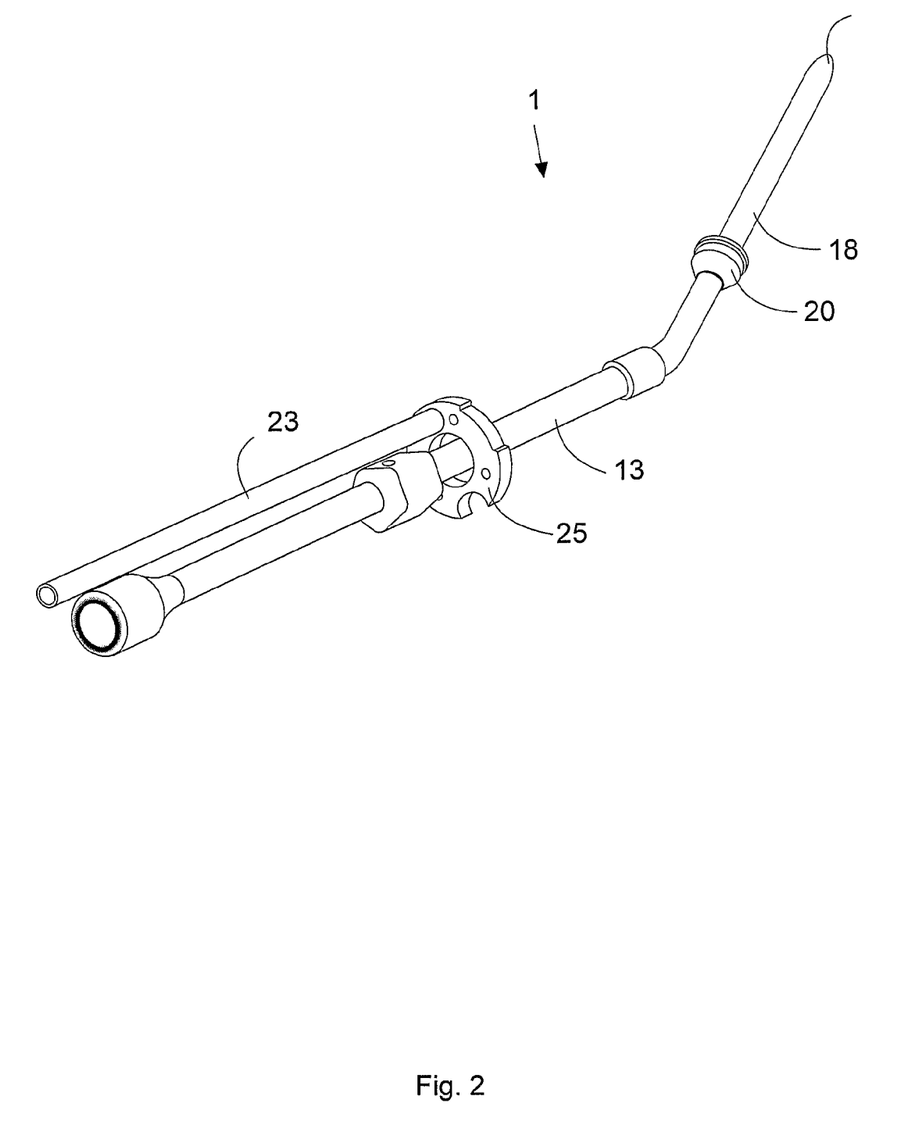
FIG. 2 an intracavitary component of an assembly according to the invention.

The intracavitary component 1, in particular an intrauterine tube 18 has a hollow insertion portion as shown in FIG. 2, which can be inserted first with its distal end 14 in a cavity, passing through the vagina canal (not shown) and cervix until cervical stopper 20 comes into contact with the cervix. The intrauterine tube 18 comprises said cervical stopper 20. Further, the intracavitary component 1 comprises a tubular element 23, which is connected to a centring ring 25. Such a tubular element 23 or a number of tubular elements 23 can be flexible and hollow and used for flushing and/or draining of the cavity.

Figure 3:
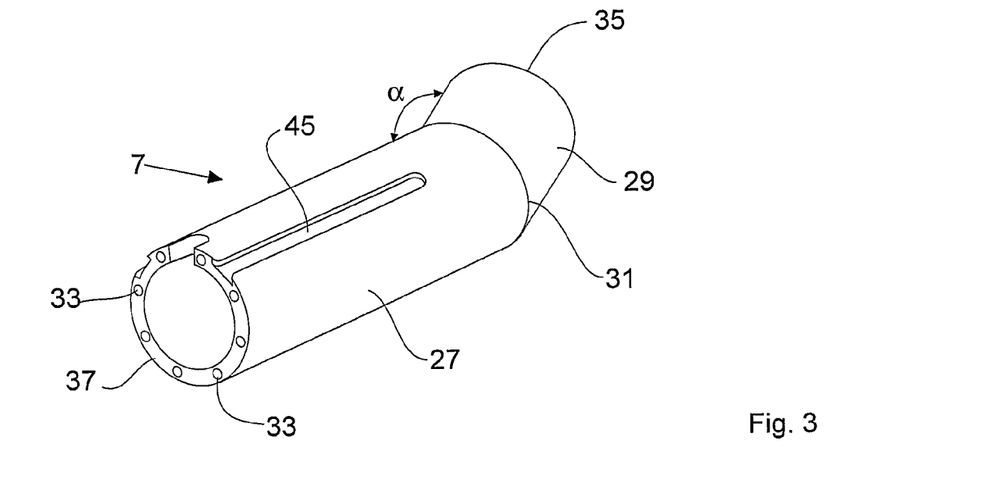
FIG. 3 a guiding unit of an assembly according to the invention.

After insertion of the intrauterine tube 18 into the vaginal canal, said guiding unit 7 is assembled from a first cylindrical part 27 and a second cylindrical part 29, wherein as shown in FIG. 3 the second part 29 forms an angle a with the first part 27. This angle a can be varied, by choosing a different second part 29, which can be detachably coupled by means of a lock 31 with the first part 27. The tubular guiding unit 7 is provided with several guides 33 for guiding an interstitial needle 5 between a proximal end 37 of the guiding unit 7 and said distal end 35. Instead of in the cylindrical wall as shown these guides 33 can also be provided along said wall of said tubular guiding unit 7.

The tubular guiding unit 7 can after assembling be placed over the intracavitary component 1. Then the tubular guiding unit 7 can be moved forward into the vaginal canal together with the intracavitary component 1 until blocked by the cervical stopper 20.

In order to locate the guiding unit 7 centrally over the intrauterine tube 18 a centering ring 25 is provided. The centering ring 25 is placed over the intrauterine tube 18 and can move axially along the intrauterine tube. The centering ring 25 is of substantially annular form, having an inner portion of the annulus which engages with the cervical stopper 20 to limit its movement in the distal direction. An outer circumference of the centring ring 25 has detent portions or other means which co-operatively engage with the inner surface of the distal end 35 of the guiding unit 7 in order to prevent rotation of the guiding unit with respect to the centring ring and limit its axial movement.

Location of the guiding unit 7 at its proximal end 37 is achieved by means of a locating collar 47 securable to the intrauterine tube 18. The locating collar is movable axially along the proximal portion of the intrauterine tube and can be secured so that it will engage a co-operating element inside the proximal end of the guiding tube 7. The locating collar 47 has a circular inner portion (although any convenient shaped hole will be suitable) and means for securing it to the intrauterine tube 18. The external shape of the locating collar in the preferred embodiment is an irregular pentagon to ensure the unambiguous orientation of the guiding unit 7 around the intrauterine tube. The proximal end 37 of the guiding unit 7 is supported by the locating collar, serving as base plate 47 (see FIG. 6b). Base plate 47 is locatable inside the guiding unit 7, its outer circumferential surface engaging the inner surface of the guiding unit. The base plate has an internal section, which in the preferred embodiment is an irregular pentagon, which cooperatively engages with locating collar 47 to provided a close non-rotational location of the base plate and hence the guiding unit around the intrauterine tube. The base plate 47 is secured to the guiding unit 7 by means of retaining screw 55'. The locating collar 47 and its cooperating element in the proximal inner surface of the guiding unit will, when correctly engaged, ensure the correct orientation of the whole assembly inside the patient. Clearly, any cooperating shapes on the collar and base plate which allow unambiguous location of the guiding unit with respect to the intrauterine tube will be suitable. This is important when treating tumours which are growing eccentrically around the internal cavity because it helps to ensure treatment is only administered to the area of the tumour.

Figure 4:
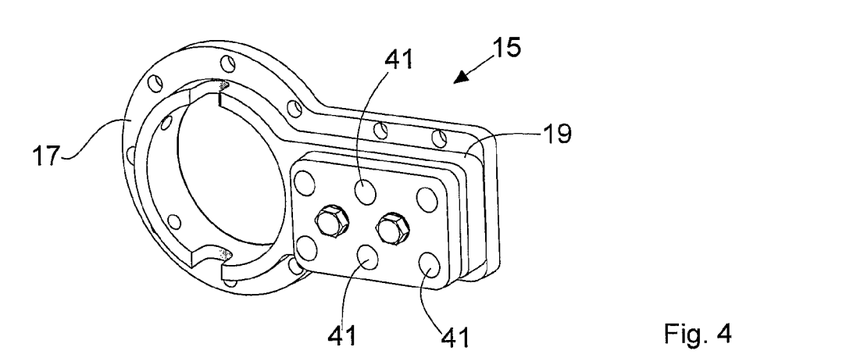
FIG. 4 a template without needles of an assembly according to the invention.

Optionally an additional perineal template 15 as shown in FIG. 4 is assembled by means of a ring 17 to the above described tubular guide 7. The perineal template 15 is provided the guiding support 19 with additional guides 41, preferably between 2-10 guides, for guiding at least one additional interstitial needle 21.

The perineal template 15 is not moved into a body cavity, but stays in contact with the guiding unit 7 completely outside the body such that the needles 21 can be passed through the skin of a patient into tumour tissue to be treated. Simultaneously, said tumour tissue can also be treated with said intracavitary component 1 and with the interstitial needles 5 of the guiding unit 7 both situated inside a cavity of a patient's body. The template 15 can be used optionally to increase the number of needles and to reach treatment sites from outside a cavity.

Figure 5:
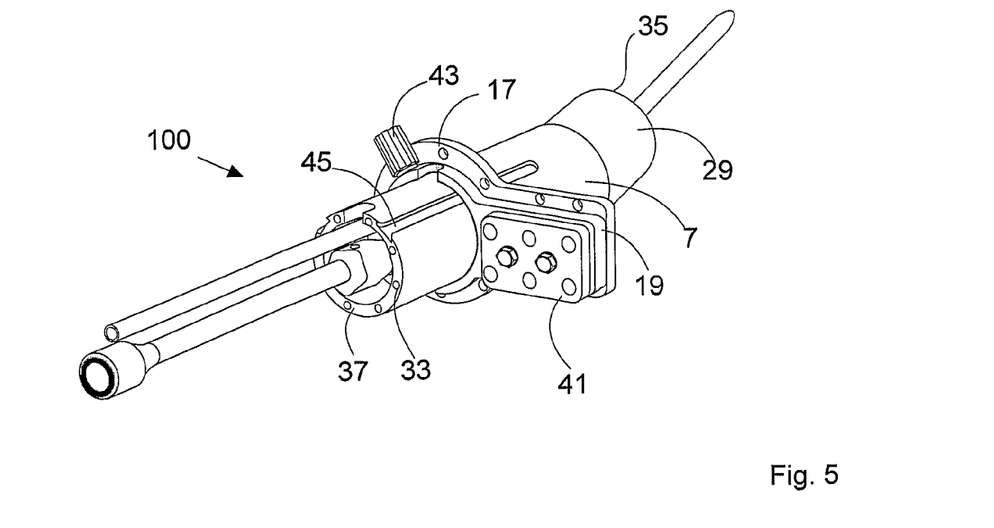
FIG. 5 an embodiment of an assembly according to the invention.
Figure 6A:
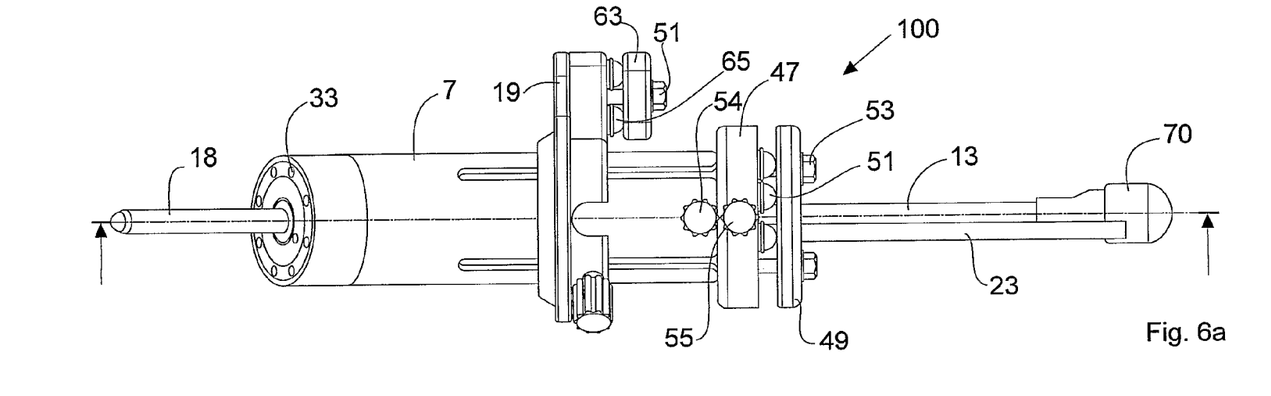
FIGS. 6a and 6b a top view, respectively a cross section of an embodiment of an assembly according to the invention.
Figure 6B:
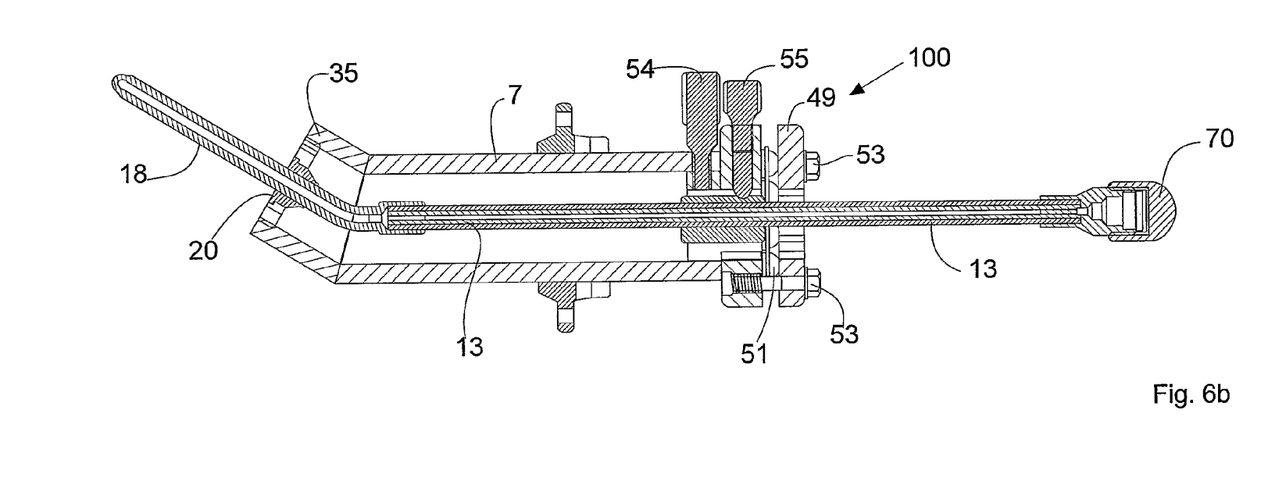

FIG. 5 shows an assembly 100 which comprises the template 15 coupled by means of the ring 17 and screws 43 in a groove 45 in the tubular guiding unit 7. A number of grooves 45 can be provided, on the tubular guiding unit 7 allowing positioning of the ring 17 before fixation.

The ring 17 can be moved rotationally and axially along the guiding unit 7 before it is fixed or secured by the screw means 43. After the assembly has been correctly placed or located, the perineal template 15 is positioned against the outer wall of the perineum. The ring 17 is provided with a number of holes 57 in the region of its circumference. Once the ring is correctly located and secured tot the guiding unit, the perineal template 15 can be sutured in place by using these holes 57. Thus the whole assembly can be secured in place after insertion, thereby ensuring accurate location of the assembly 100 with respect to the tumour for the duration of the treatment. This is important when planning and conducting the treatment to ensure the radiotherapy dose is administered in the correct dose and location.

Then the base plate 47 together with a cover plate 49, retaining pellets 51 and fixing screws 53 are assembled (FIGS. 6a and 6b). The assembled base plate 47 is centred and coupled by screws 54, 55 to guiding unit 7.

The needles 5, 21 can be made of bio-compatible plastic material, composite material or titanium. In the assembly as shown in FIGS. 6a and 6b needles 5 with or without the help of obturators (not shown) are inserted through guiding holes in the cover plate 49, retaining pellets 51, base plate 47 and guides 33.

Before assembling the assembly 100 the position of every needle 5 on the proximal side is marked, when the distal point of the needle 5 is in line with the distal end 35 of the tubular part 29. Then the desired depth of the needle 5 in the patient tissue is determined by reference to a separate procedure to determine the size and location of the tumour tissue, and a second mark on the needle 5 is made. Thereafter, the needles 5 are removed from the guides 33 and for every needle 5 its needle position in the guiding unit 7 has to be remembered. After assembling the assembly as shown in FIGS. 6a and 6b needles 5 can be placed in the correct position.

These needles 5 can be locked in position by tightening screws 53 with a screwdriver (not shown) such that the retaining pellets 51 compress and secure the needles 5 against longitudinal movement.

Additional needles 21 can be placed in the support 19, wherein the locking of said needles is performed in the same way by means of screws 61, a clamping plate 63 and retaining pellets 65.

The intrauterine tube 18 is at least partly hollow and can be provided with a marker. Further, markers (not shown) are inserted into the hollow needles 5, 21 for assisting in forming an image of the tumour tissue for treatment planning purposes.

With the assembly 100 according to the invention placement of the needles 5 can be done at any moment without requiring considerable skills of an operator, as the proximal end of the guides 33 is in normal use always positioned outside the body and therefore easily accessible by the operator.

Parts fabricated from plastic material such as the needles 5 or the guiding unit 7 may be provided with markers (not shown) for making the assembly Computed Tomography (CT) and/or Magnetic Resonance Imaging (MRI) compatible.

The centring ring 25 can be provided with an outlet and connected to conduits such as tube 23 to provide a flushing facility. Flushing liquid is passed into the assembly through tube 23, and it passes out of the end of the tube into the cavity areas. A drain hole may be located in the centering ring 25 through which draining fluid can pass back into the guiding unit 7. Exit means can be located in the base plate 47 through which waste or exudate can pass to be safely disposed of.

Figure 7A:
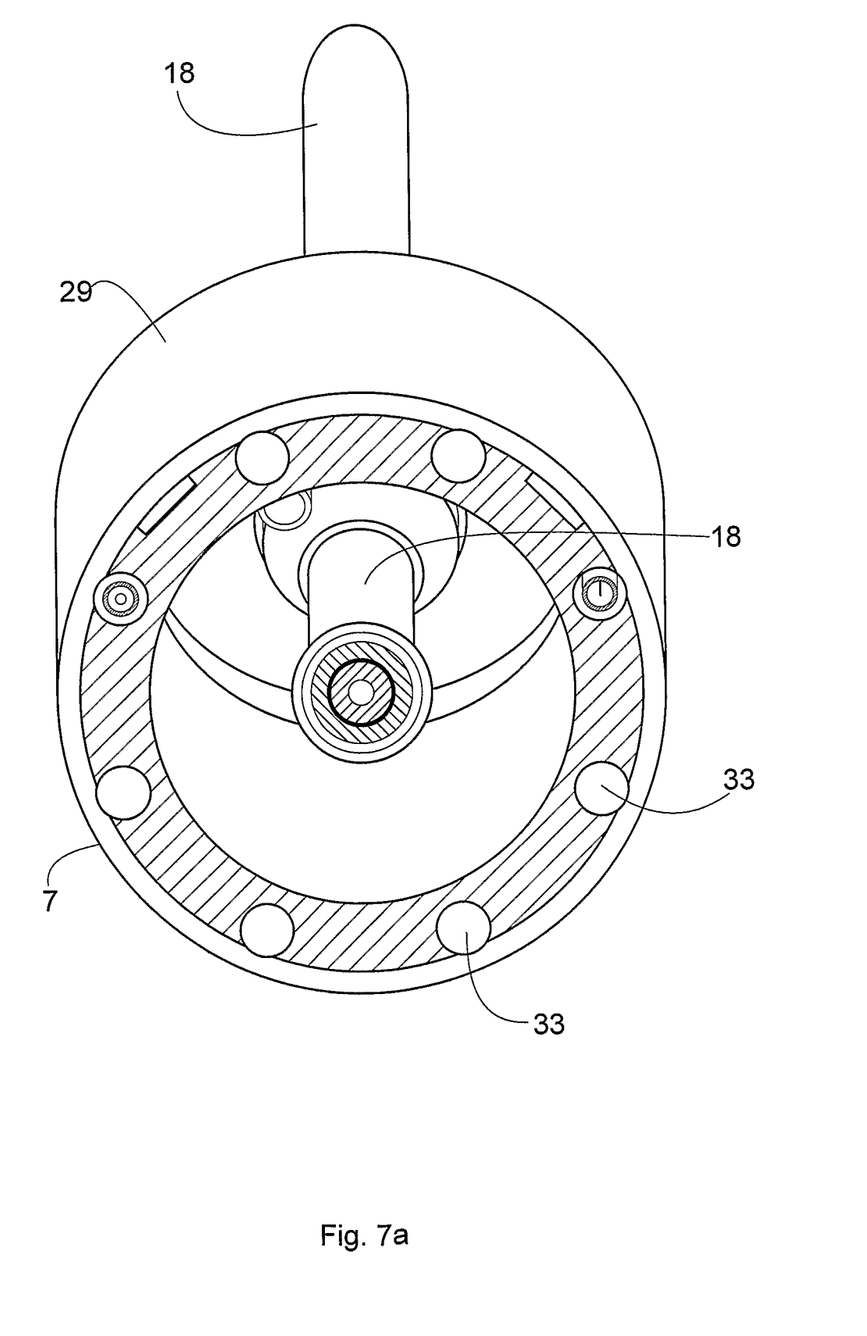
FIGS. 7a and 7b are cross-sections through a guide unit along the line 7-7 shown in FIG. 3 of two alternative forms of guiding unit.

In an alternative embodiment the guiding unit 7 can be made in a cylindrical shape but with a waisted zone in the central area. The waisted constriction 8 is located in the central region of the guiding unit 7 and is of smaller diameter than the proximal 35 and distal end 37 of the guiding unit. This is advantageous in making the cleaning and sterilisation of the guides 33 easier between uses of the assembly 100 because the enclosed length of the guides 33 along which the needles 5 pass is considerably reduced. FIG. 7a shows a cross-section of the guiding unit 7.

Figure 7B:
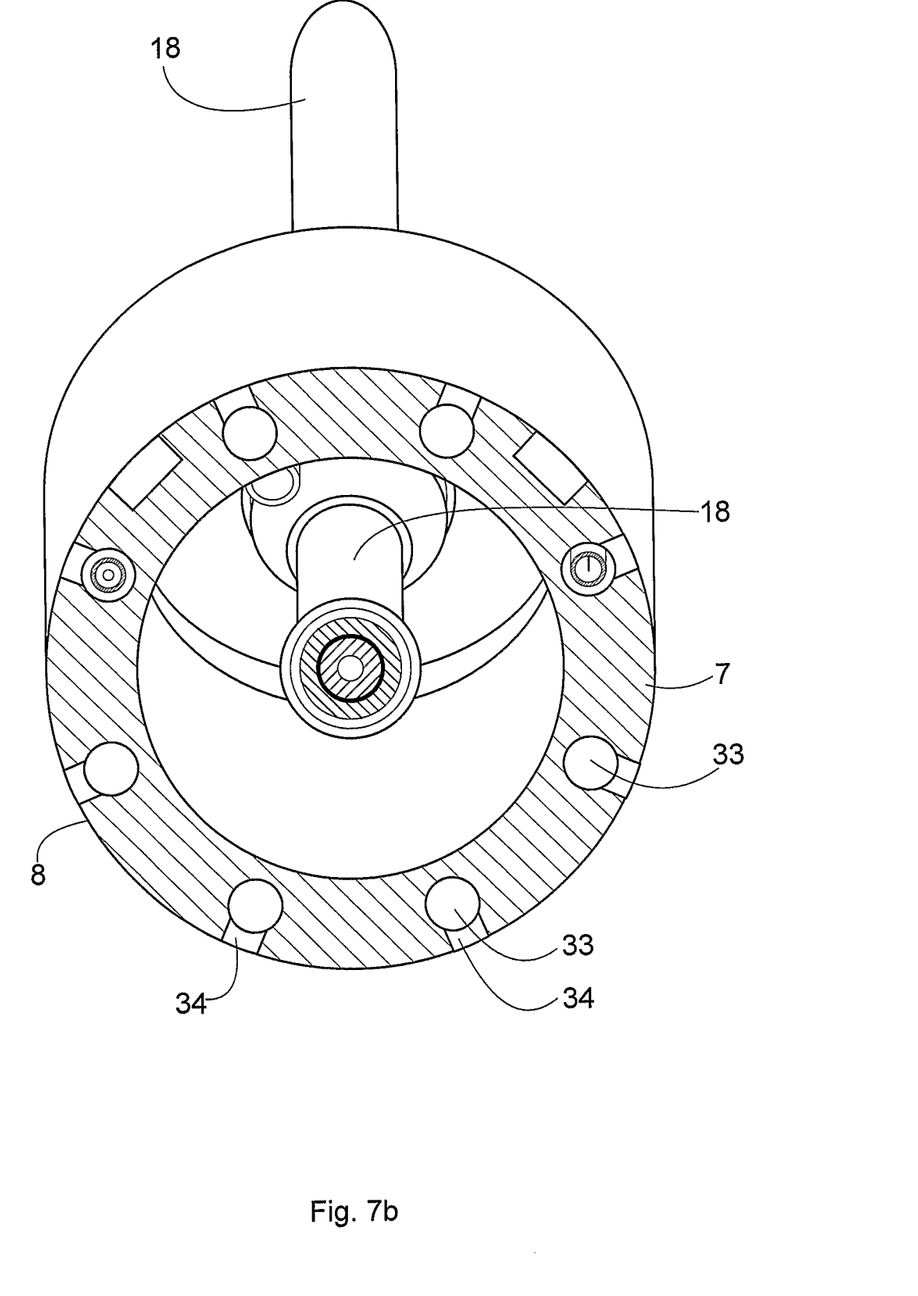

FIG. 7b shows a cross-section of the waisted central area 8 in which the external diameter of the guiding unit 7 is reduced. The open channel section 34 of the guides 33 can be seen. Clearly it will be much easier to clean and sterilize an open channel than the enclosed guides 33. However, in some applications there will be advantages to maintaining a closed guide 33.

This instrument is normally uses in combination with an afterloader which provides the radioactive sources of treatment. A preferred radioactive source is Iridium 192.

Whilst the assembly has been described for treatment with uterine or cervical cancer, there is no reason why the assembly 100 could not be used to treat cancers accessible through another body cavity, such as cancer of the rectum or colon. In such cases some minor adaptations to the geometry of some of the components might be required but the underlying principals of operation could remain unchanged.

Figure 8:
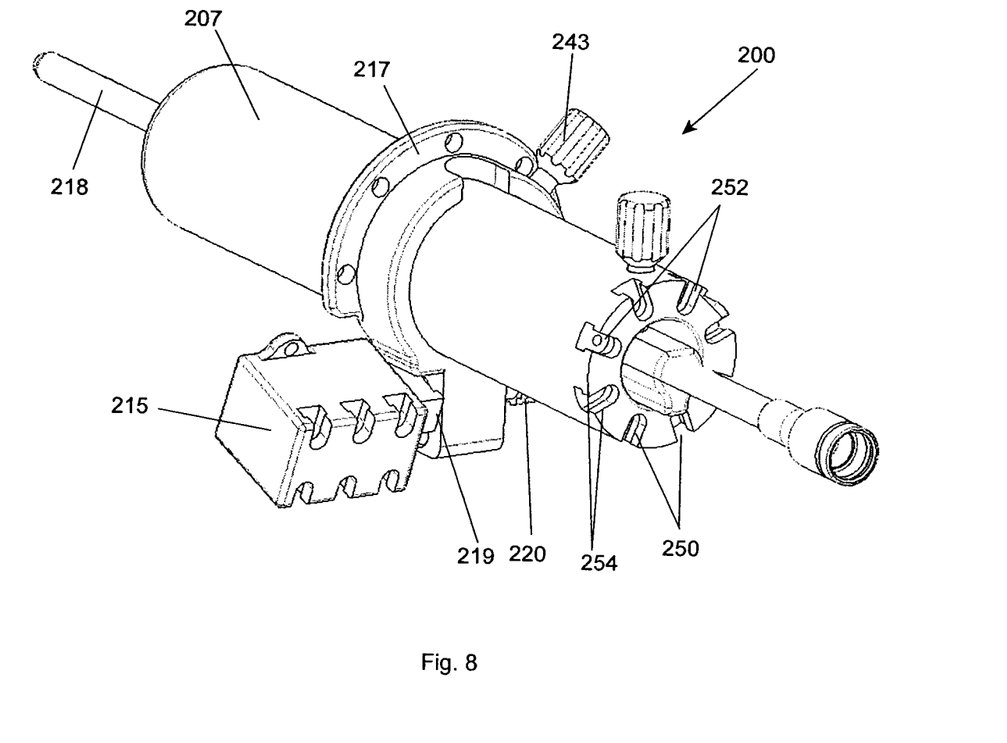
FIGS. 8-9-10a-10b are detailed views of an alternative embodiment of an applicator according to the invention.

FIG. 8 shows an alternative embodiment of an applicator according to the invention. In this embodiment the applicator 200 is shown with a straight guide tube 207. The perineal template 215 is mounted on the guiding tube assembly and supported by an annular ring 217. The perineal template 215 is pivotally mounted on the annular ring 217. This pivoting function enables the angle of the longitudinal axis of any needles supported by the perineal template to be varied with respect to the longitudinal axis of the guide tube 207. Advantageously, this enables the clinician to place any extra needles supported by the template at an optimum angle and position in the patient in order to treat a tumour which may be either outside the vaginal canal or on its outer tissue walls.

Pivot means (not shown in detail) are provided with securing or clamping means 220 which can be used to secure the annular ring 217 to the perineal template 215 to prevent or at least minimise rotational movement of the template with respect to the guide tube once the desired angle between the components has been set.

In this embodiment the template 215 can also be moved axially along the guide tube and rotated around it as desired. Preferably a screw or other similar clamping means 243 is provided to secure the annular ring 217 in place.

Figure 9:
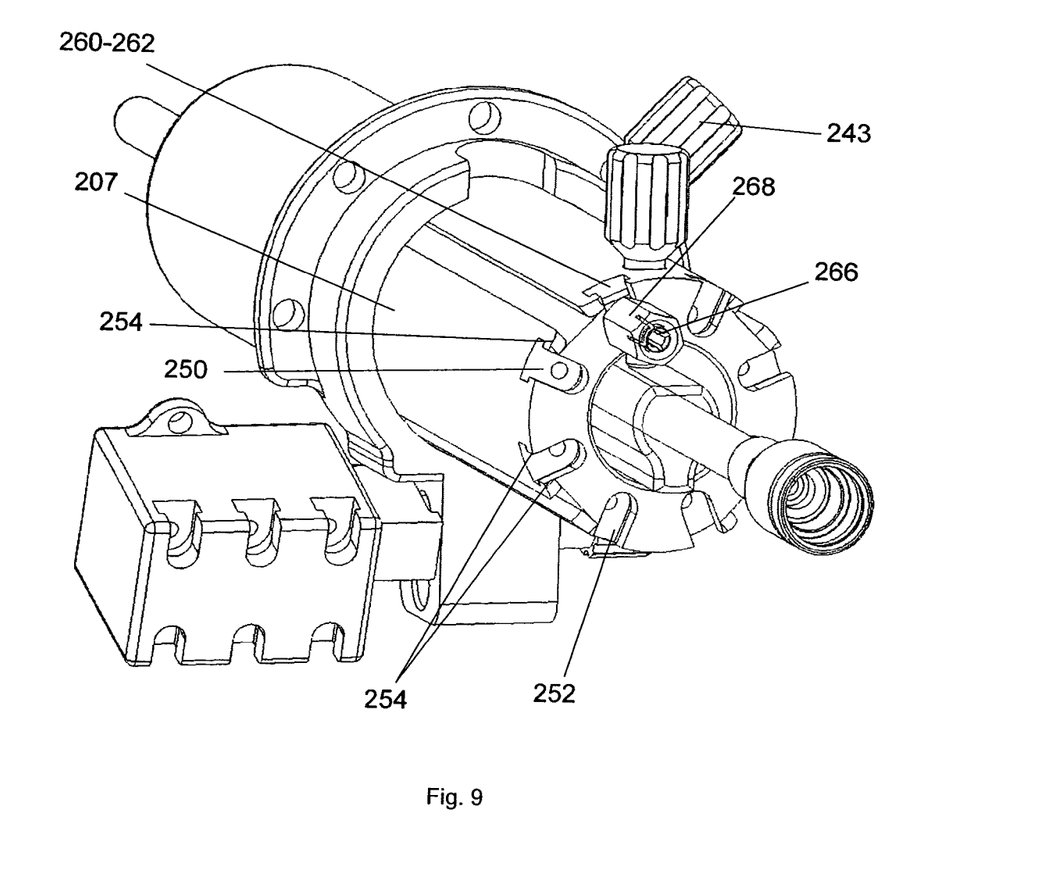

FIG. 9 shows an alternative means for placing and securing the needles. The guide tube 207 is provided with a radially extending retaining channel 250 which preferably has an open end 252 extending radially outward from the central region of the tube. The channel 250 is provided with retaining shoulders 254 which can be used to retain a supporting boot element 260 through which a needle can be passed. It will be apparent that although the retaining channel 250 is shown extending in a radial direction, it is also perfectly feasible that the channel could extend tangentially, or in a curved path or another convenient path along which the sole portion of the needle gripping boot can slide in order to engage with the retaining shoulders 254.

Figure 10A:
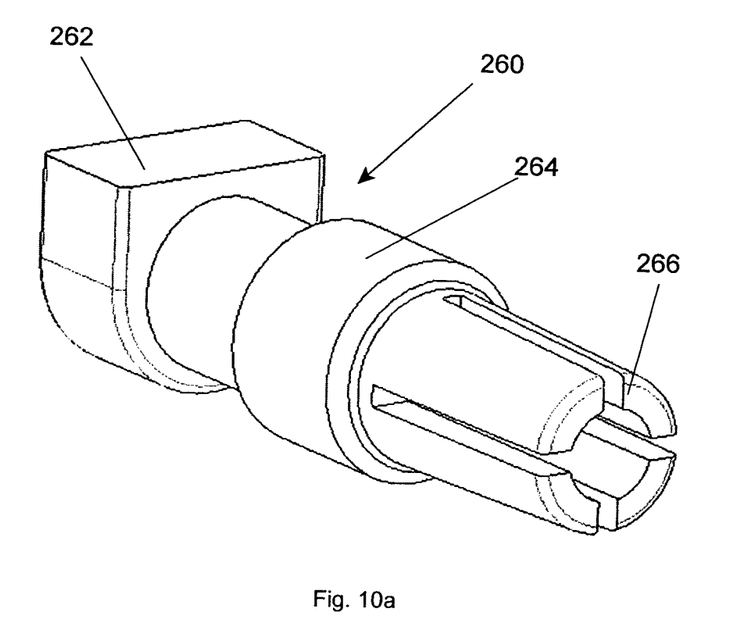
Figure 10B:
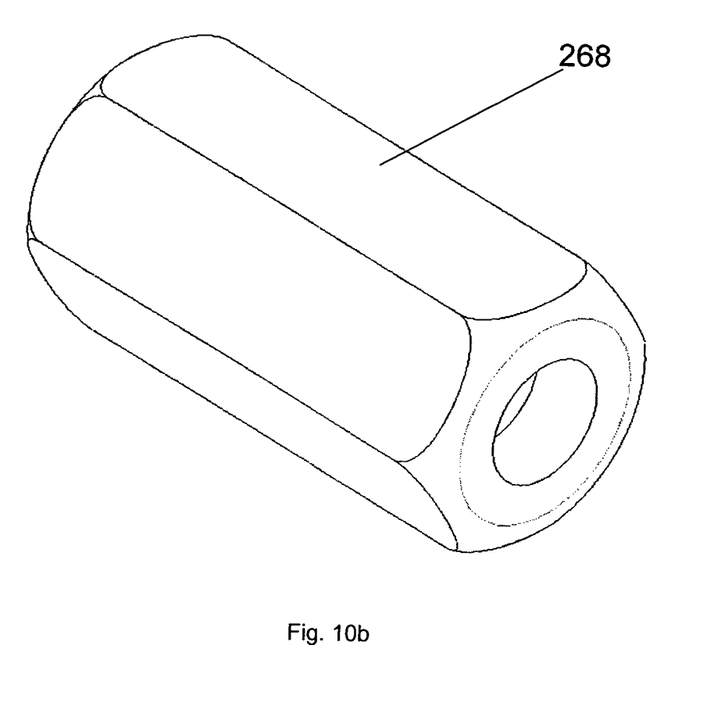

FIGS. 10a-b shows the supporting boot element 260. The supporting boot element 260 has a sole plate 262 of greater footprint area than the body 264 of the boot element 260. The sole plate 262 can be located in the channel 250 by a transverse sliding motion and is retained by the shoulders 254, which extend partly across channel 250 acting on two sides of the sole plate which extend substantially parallel to each other. Sole plate 262 has a sole face which defines a hole through which a needle can pass. The upper body part of the boot element 264 includes a compressible section 266 which can grip a needle passing through it. Additionally, a clamping means can be mounted on the body portion to further clamp the needle against longitudinal movement.

In another non-depicted embodiment the sole plate 262 of the boot element 260 can be manufactured from a deformable material, like a rubber, and positioned in a channel in such manner that the deformable sole plate clamps or presses itself against the (inner) side walls of the channel, such that movement of the sole plate 262 in a longitudinal direction is prevented. In this embodiment the channel in which the deformable sole plate 262 is positioned can be configured as an open channel without retaining shoulders.

The compressible section 266 and clamping means 268 can be of a known type of construction and act in the manner of a gland nut assembly with, for example, co-operating threaded portions which can be tightened and clamped onto the needle and secure the needle against longitudinal movement because it is attached to the sole plate which is snugly mounted in the channel 250. The clamping means 268 can be made like a gland nut and can have either a knurled outer surface or conventional parallel flat faces which can be tightened by means of a spanner.

Whilst the sole plate 262 is shown as having parallel sides and a "U" shaped nose portion which is innermost on the retaining channel, it is quite feasible and practical to provide it with sides which are tapered (or have a tapered shape) and have a "V" shape, providing the channel 250 is also shaped in a complimentary manner.

Similar arrangements and variations can be used in the perineal template for securing any needles supported by it against longitudinal movement.

This principle of securing the needles has the advantage that the applicator can be easily assembled before insertion into the patient, and the clamping means 268 can be partially tightened to lightly secure the needles against movement during any remaining assembly and insertion process before the needles are fully clamped prior to the actual treatment. This allows some movement or adjustment of the needles if necessary and so helps to prevent damage to the needles or unnecessary injury to the patient.

The invention claimed is:

1. Assembly for performing brachytherapy treatment of tumour tissue in an animal body, the assembly comprising:
   an intracavitary component;
   a guiding unit which is connected to the intracavitary component such that the guiding unit extends at least partly parallel with the intracavitary component, wherein
   the guiding unit having a tubular structure including a lumen formed within the guiding unit, the guiding unit having a length from a proximal end to a distal end thereof, the length being sufficient such that in use the proximal end of the guiding unit is configured to be situated outside the animal body to be treated, while the distal end of the guiding unit is configured to be situated in a cavity of the animal body, wherein
   the guiding unit includes at least one guide formed in the guiding unit and extending from the proximal end of the guiding unit to the distal end of the guiding unit, the at least one guide being configured to receive a corresponding first needle element for delivering treatment to the tumour tissue; and
   a template coupled to the guiding unit, the template being configured to receive at least one second needle element;
   wherein the at least one guide is configured to receive the first needle element while the intracavitary component is positioned in the cavity of the animal body and the template is coupled to the guiding unit.

2. The assembly according to claim 1, wherein the guiding unit comprises a first part and a second part, wherein the second part forms an angle with the first part.

3. The assembly according to claim 2, wherein the first and second part of the guiding unit are detachably coupled with each other.

4. The assembly according to claim 2, wherein the first needle element is curved and has an angle similar to the angle between the first part and the second part of the guiding unit.

5. The assembly according to claim 1, wherein the first and second needle elements are made of at least one of plastic material, metal, and composite material.

6. The assembly according claim 1, wherein the template is detachably coupled to the guiding unit, the template being provided with a guiding support for receiving the at least one second needle element.

7. The assembly according claim 1, wherein at least parts of the assembly are provided with markers for making the assembly at least one of Computed Tomography (CT) and Magnetic Resonance Imaging (MRI) compatible.

8. The assembly according claim 1, wherein the guiding unit and the template are configured to receive a plurality of first needle elements and a plurality of second needle elements respectively, and wherein each of the plurality first and second needle elements can be operated independently from each other.

9. The assembly according to claim 1, wherein the guiding unit is arranged centrally over the intracavitary component and wherein a distal end of the intracavitary component is distally elongated relative to said guiding unit.

10. The assembly according to claim 1, wherein the guiding unit is provided with at least one conduit for one of flushing and draining a treatment site.

11. A guiding unit for performing brachytherapy treatment of tumour tissue in an animal body comprising:
    a tubular member having a lumen extending from a proximal end to a distal end thereof, the tubular member being disposed about an intracavitary component, and having a length such that in use the proximal end of the tubular member is situated outside the animal body, while the distal end of the tubular member is situated in a cavity of the animal body,
    the tubular member including at least one guide formed in the tubular member and extending between the proximal and distal ends,
    the at least one guide being configured to receive a corresponding first needle element for treating the tumour tissue,
    wherein the tubular member is configured to be coupled to a template for receiving at least one second needle element for treating the tumour tissue, and
    wherein the at least one guide is configured to receive the first needle element when the intracavitary component is positioned in the cavity of the animal body for treatment of the tumour and the template is coupled to the tubular member.

12. Method for performing brachytherapy treatment of tumour tissue in an animal body, the method comprising:
    assessing at least one tumour;
    inserting an intracavitary component at least partly in a body cavity near the tumour;
    connecting a guiding unit with the intracavitary component for forming an assembly, the guiding unit including a tubular member having a lumen extending from a proximal end to a distal end thereof, the tubular member having a length such that in use the proximal end of the tubular member is situated outside the animal body, while the distal end of the tubular member is situated in the body cavity, the tubular member including at least one guide formed in the tubular member and extending between the proximal and distal ends, the at least one guide being configured to receive a corresponding first needle element for delivering treatment to the tumour;
    inserting the assembly further into the cavity such that the assembly is in a position for treatment of the tumour;

coupling a template to the guiding unit for receiving at least one second needle element for delivering treatment to the tumour; and inserting the first needle element through the at least one guide while the intracavitary component is positioned in the cavity for treatment of the tumour and the template is coupled to the guiding unit.

13. The method according to claim 12, further including positioning the template outside the body, inserting the at least one second needle element into the skin via the template, and further inserting the at least one second needle element into the tumour.

* * * * *

UNITED STATES PATENT AND TRADEMARK OFFICE
CERTIFICATE OF CORRECTION

| | | |
|---|---|---|
| PATENT NO. | : 8,834,339 B2 | Page 1 of 1 |
| APPLICATION NO. | : 13/120282 | |
| DATED | : September 16, 2014 | |
| INVENTOR(S) | : Jean-Michel Hannoun-Levi et al. | |

It is certified that error appears in the above-identified patent and that said Letters Patent is hereby corrected as shown below:

In the Claims

Claim 8, Col. 10, Line 16, "plurality first" should read as --plurality of first--.

Signed and Sealed this
Third Day of March, 2015

Michelle K. Lee
*Deputy Director of the United States Patent and Trademark Office*